United States Patent
Alferness et al.

(10) Patent No.: US 8,109,912 B2
(45) Date of Patent: Feb. 7, 2012

(54) WEARABLE INFUSION ASSEMBLY

(75) Inventors: Clifton A. Alferness, Port Orchard, WA (US); John McKenzie, San Carlos, CA (US)

(73) Assignee: Calibra Medical, Inc., Redwood City, CA (US)

(*) Notice: Subject to any disclaimer, the term of this patent is extended or adjusted under 35 U.S.C. 154(b) by 316 days.

(21) Appl. No.: 12/209,965

(22) Filed: Sep. 12, 2008

(65) Prior Publication Data
US 2010/0069848 A1 Mar. 18, 2010

(51) Int. Cl.
*A61M 5/00* (2006.01)
(52) U.S. Cl. .......................................... 604/181
(58) Field of Classification Search ............... 604/181
See application file for complete search history.

(56) References Cited

U.S. PATENT DOCUMENTS

| | | | |
|---|---|---|---|
| 4,666,434 A * | 5/1987 | Kaufman | 604/179 |
| 4,846,807 A * | 7/1989 | Safadago | 604/179 |
| 4,935,013 A * | 6/1990 | Haber et al. | 604/192 |
| 5,037,398 A * | 8/1991 | Buchanan | 604/180 |
| 5,152,753 A | 10/1992 | Laguette et al. | |
| 6,086,564 A * | 7/2000 | McLaughlin | 604/179 |
| 6,126,637 A * | 10/2000 | Kriesel et al. | 604/132 |
| 6,565,533 B1 * | 5/2003 | Smith et al. | 604/144 |
| 6,626,884 B1 * | 9/2003 | Dillon et al. | 604/409 |
| 7,198,616 B2 * | 4/2007 | Mossanen-Shams et al. | 604/174 |
| 2003/0050623 A1 | 3/2003 | Lord et al. | |
| 2003/0225427 A1 * | 12/2003 | Chen | 606/162 |
| 2005/0065466 A1 | 3/2005 | Vedrine | |
| 2005/0131353 A1 * | 6/2005 | Mossanen-Shams et al. | 604/179 |
| 2005/0148889 A1 * | 7/2005 | Chen | 600/509 |
| 2005/0277887 A1 | 12/2005 | Douglas et al. | |
| 2006/0200073 A1 * | 9/2006 | Radmer et al. | 604/93.01 |
| 2007/0049865 A1 * | 3/2007 | Radmer et al. | 604/93.01 |
| 2007/0287960 A1 | 12/2007 | Adams et al. | |
| 2008/0058772 A1 | 3/2008 | Robertson et al. | |
| 2009/0088682 A1 * | 4/2009 | Cross et al. | 604/38 |
| 2009/0088694 A1 * | 4/2009 | Carter et al. | 604/151 |
| 2009/0259182 A1 * | 10/2009 | Cross et al. | 604/151 |
| 2010/0069848 A1 * | 3/2010 | Alferness et al. | 604/151 |

FOREIGN PATENT DOCUMENTS

| | | |
|---|---|---|
| EP | 0461680 A2 | 12/1991 |
| JP | 2004024699 A | 1/2004 |

OTHER PUBLICATIONS

Korean Intellectual Property Office (ISA/KR), International Search Report Mailed Mar. 25, 2010, for International Patent Application No. PCT/US2009/056619 (5 pages).

\* cited by examiner

*Primary Examiner* — Jackie Ho
*Assistant Examiner* — Diva Ranade
(74) *Attorney, Agent, or Firm* — Richard O. Gray, Jr.; Graybeal Jackson LLP

(57) ABSTRACT

A wearable liquid medicament delivery assembly comprises a band arranged to at least partially encircle and be secured to a body extremity of a wearer and a liquid medicament delivery device carried by the band. The device includes a reservoir arranged to hold the liquid medicament, a piercing member arranged to penetrate the skin of the wearer to deliver the liquid medicament, and a pump that pumps the liquid medicament from the reservoir to the piercing member to thereby cause the liquid medicament to be delivered to the wearer.

28 Claims, 3 Drawing Sheets

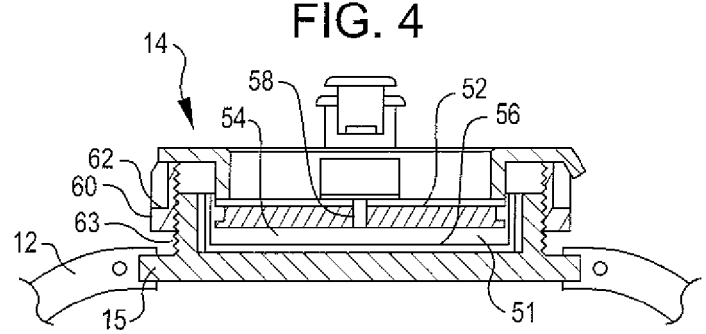
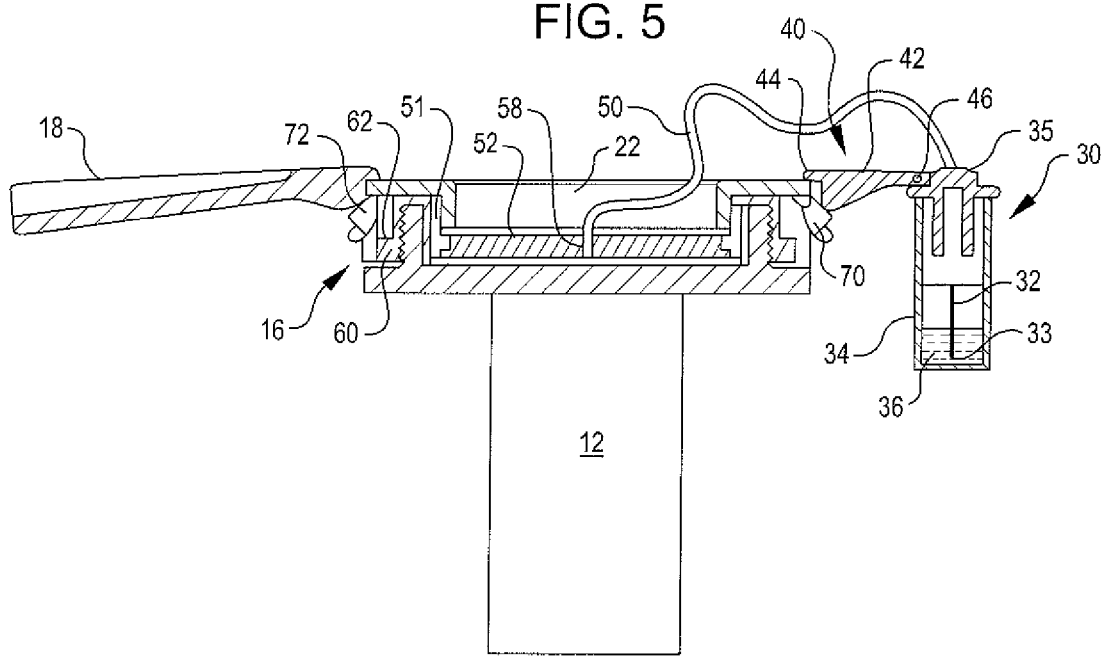

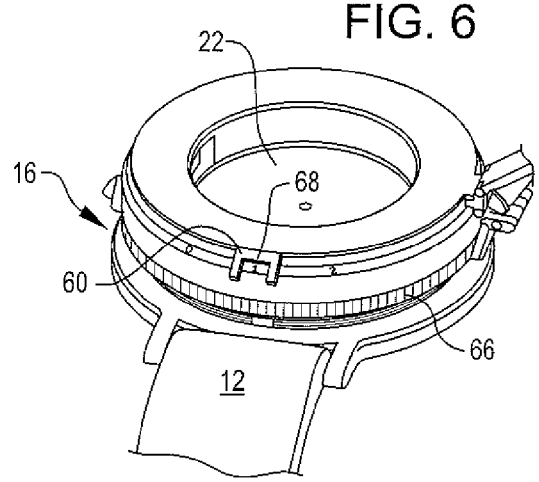
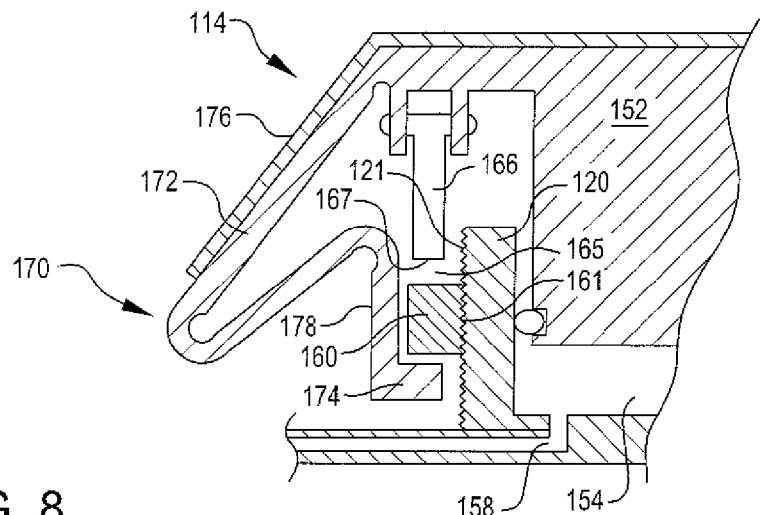
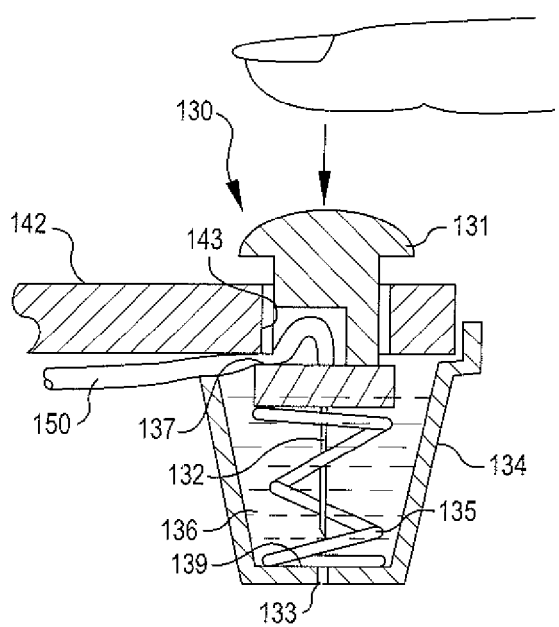

WEARABLE INFUSION ASSEMBLY

BACKGROUND OF THE INVENTION

The present invention relates to infusion devices and more particularly to such devices that enable liquid medicaments to be conveniently and safely self-administered by a patient.

Administration of insulin has traditionally been accomplished using a syringe. Recently, needle carrying pen-like devices have also been employed for this purpose. Both forms of insulin administration require the patients to stick themselves each time they inject insulin, often many times a day. Thus, these traditional forms of insulin administration have been a rather pervasive intrusion in the lives and routines of the patient's who have had to adopt and employ them.

More recently, insulin pumps attached by tubing to an infusion set mounted on the patient.'s skin have been developed as an alternative form of insulin administration. Such pumps may be controlled by a programmable remote electronic system employing short range radio communication between a control device and electronics that control the pump. While such devices may involve fewer needle sticks, they are expensive to manufacture. They are also complex to operate and cumbersome and awkward to wear. Further, the cost of such devices can be many times the daily expense of using a traditional injection means such as a syringe or an insulin pen.

Devices of the type mentioned above also require a significant amount of training to control and thus use the devices. Great care in programming the devices is required because the pumps generally carry sufficient insulin to last a few days. Improper programming or general operation of the pumps can result in delivery of an excessive amount insulin which can be very dangerous and even fatal.

Many patients are also reluctant to wear a pump device because they can be socially awkward. The devices are generally quite noticeable and can be as large as a pager. Adding to their awkwardness is their attachment to the outside of the patients clothes and the need for a catheter like tubing set running from the device to an infusion set located on the patient's body. Besides being obvious and perhaps embarrassing, wearing such a device can also be a serious impediment to many activities such as swimming, bathing, athletic activities, and many activities such as sun bathing where portions of the patient's body are necessarily uncovered.

In view of the above, a more cost effective and simple device has been proposed whereby an injection system is discreetly attached directly to the skin of the patient. The device may be attached to the patient under the patient's clothing to deliver insulin into the patient by the manual pumping of small doses of insulin out the distal end of a temporarily indwelling cannula that is made a part of the pump device. The cannula may be made a part of the drug delivery device before, during or after the attachment of the drug delivery device to the skin of the patient. The device may be made quite small and, when worn under the clothes, entirely unnoticeable in most social situations. It may still carry sufficient insulin to last a patient several days. It can be colored to blend naturally with the patient's skin color so as not to be noticeable when the patient's skin is exposed. As a result, insulin for several days may be carried by the patient discreetly, and conveniently applied in small dosages after only a single needle stick. For a more complete description of devices of this type, reference may be had to co-pending application Ser. No. 11/906,130, filed on Sep. 28, 2007 for DISPOSABLE INFUSION DEVICE WITH DUAL VALVE SYSTEM, which application is owned by the assignee of this application and hereby incorporated herein by reference in its entirety.

The present invention provides an alternative to the devices disclosed in the above referenced co-pending application that may be preferable to some patients in some situations. More particularly, the devices disclosed herein provide excellent patient safety and/or convenience. For example, in embodiments of the invention described herein, the devices are attached to a band that is worn by a patient wherein, a needle for delivering the liquid medicament is deployed to pierce the skin only when a dosage of liquid medicament is to be delivered. Hence, the band may be removed at any other time with the ease of removing a wrist watch. Further, in some embodiments, when the needle is not used to deliver the liquid medicament, it is retracted into a device body and covered by a pivoted cover for safe and sterile keeping. Still further, in some embodiments, a desired volume of medicament to be delivered may be selected and after delivery, the volume of the delivered dosage is indicated by the device. In still further embodiments, the amount of dosage delivered is indicated. These and other advantages are addressed herein.

SUMMARY OF THE INVENTION

According to one embodiment, a wearable liquid medicament delivery assembly comprises a band arranged to at least partially encircle and be secured to a body extremity of a wearer and a liquid medicament delivery device carried by the band. The device includes a reservoir arranged to hold the liquid medicament, a piercing member arranged to penetrate the skin of the wearer to deliver the liquid medicament, and a pump that pumps the liquid medicament from the reservoir to the piercing member to thereby cause the liquid medicament to be delivered to the wearer.

The device may include a needle assembly including the piercing member. The piercing member may be a needle. The device may include a mounting for the needle assembly. The mounting may be arranged to deploy the needle prior to each liquid medicament delivery and to retract the needle after each liquid medicament delivery. The needle assembly may include a source of antiseptic that maintains the needle in a sterile condition. The needle assembly may also include a collapsible boot that houses the needle. The collapsible boot may contain the source of antiseptic.

The device is preferably attachable to the band. The device may further include a dosage selector that adjusts the device to deliver a selectable volume of liquid medicament. The dosage selector may be arranged to retain an indication of the selected volume after liquid medicament delivery. The dosage sector may include a latch that retains an indication of the selected volume after liquid medicament delivery.

The device may further include a safety valve that precludes liquid medicament flow to the piercing member until the piercing member has penetrated the skin and has been deployed. The device may further include a flexible conduit coupling the reservoir with the piercing member.

In another embodiment, a wearable liquid medicament delivery assembly comprises a liquid medicament delivery device including a reservoir arranged to hold the liquid medicament, a needle arranged to penetrate the skin of the wearer to deliver the liquid medicament, and a pump that pumps the liquid medicament from the reservoir to the piercing member to thereby cause the liquid medicament to be delivered to the wearer. The assembly further includes a band arranged to be secured to a body of a wearer and to carry the device.

The device may include a housing secured to the band. The needle may be enclosable within the housing and releasable from the housing for liquid medicament delivery to the wearer. The device may further include a cover arranged to cover the housing with the needle enclosed therein and to open to permit release of the needle for liquid medicament delivery to the wearer. The device may further include a mount having a distal end supporting the needle and a proximal end hingedly connected to the body to permit the needle to pivot from an enclosed position within the device body to a ready position for liquid medicament delivery to the wearer. The needle may be arranged to be displaced from the ready position to a delivery position penetrating the skin of the wearer for the delivery of liquid medicament to the wearer.

The device may further includes a collapsible boot encircling the needle. The device may further include a flexible conduit coupling the reservoir with the needle. The device may further include a safety valve that precludes liquid medicament flow to the needle until the needle has penetrated the skin. The safety valve may be arranged to pinch the flexible conduit closed to preclude liquid medicament flow to the needle until the needle has penetrated the skin.

The device may further include a dosage selector that adjusts the device to deliver a selectable volume of liquid medicament. The device may further include a dosage indicator that provides an indication of a total amount of liquid medicament delivered.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 4 is a sectional view of the assembly of FIG. 1 taken along lines 4-4 of FIG. 1;

FIG. 5 is a sectional view taken along lines 5-5 of FIG. 3;

FIG. 6 is a perspective view of the infusion assembly of FIG. 1 to an enlarged scale illustrating a dosage counter thereof according to one embodiment of the present invention;

FIG. 7 is a partial sectional side view illustrating the infusion device of another infusion assembly according to another embodiment of the invention; and FIG. 8 is a sectional side view illustrating an alternative needle assembly that may be employed in the assembly of FIGS. 1-6 according to a further embodiment of the invention.

DETAILED DESCRIPTION OF THE INVENTION

Figure 1:
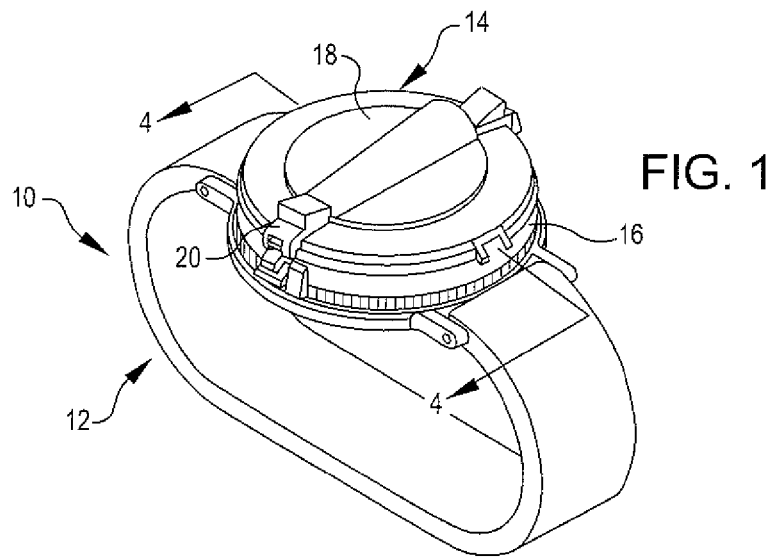
FIG. 1 is a perspective view of an infusion assembly according to one embodiment of the present invention.

Referring now to FIG. 1, it is a perspective view of an infusion assembly 10 according to one embodiment of the present invention. The assembly 10 generally comprises a band 12 arranged to at least partially encircle and be secured to a body extremity, such as an arm or wrist and a liquid medicament delivery device 14 secured to the band 12. The device 14 is preferably attachable to and detachable from the band 12. Also, the band 12 may be adjustable to permit convenient repositioning of the assembly 10 on the body extremity.

The liquid medicament delivery device 14 may deliver, for example, insulin to the wearer. It includes a cylindrically shaped case or housing 16 having and a cover 18 that is connected to the housing 16 by a hinge 20.

Figure 2:
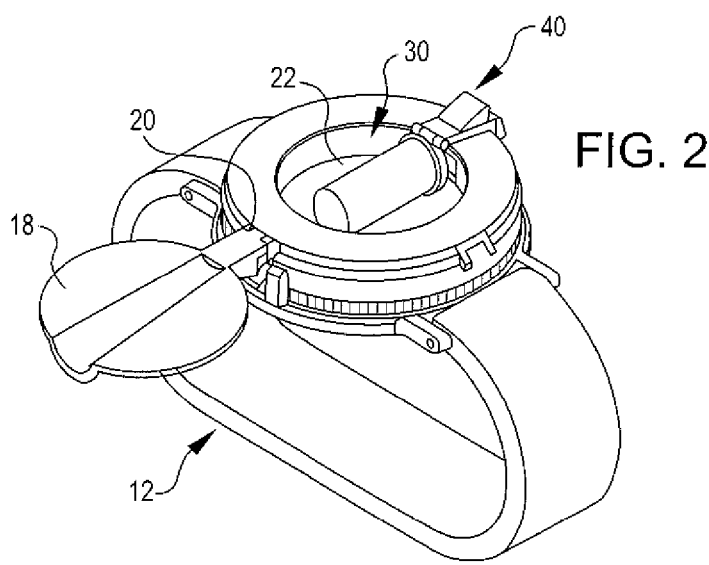
FIG. 2 is a perspective view of the assembly of FIG. 1 being made ready to provide a dose of medication.
Figure 3:
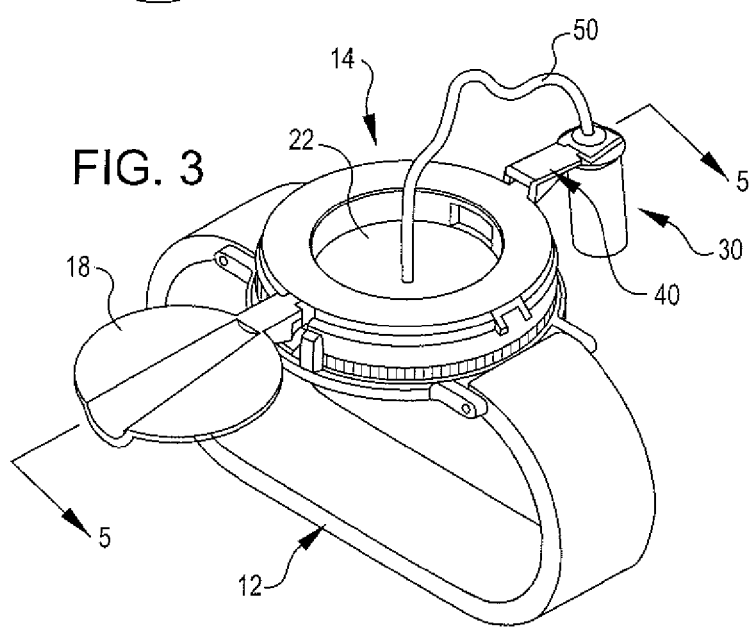
FIG. 3 is a perspective view of the assembly of FIG. 1 ready to provide a dose of medication.

As may be seen in FIG. 2, when the cover is opened, an inner chamber 22 is exposed in which a needle assembly 30 is stored for medicament delivery. The needle assembly 30 is mounted to the case by a mounting arrangement 40 that disposes the needle assembly for medicament delivery on demand. The mounting arrangement 40, as may be best seen in FIG. 5, includes an arm 42 coupled at one end to the case 16 by a first hinge 44 and to the needle assemble 30 by a second hinge 46. The arm 42 aligns the needle assembly 30 with the skin as the needle assembly 30 is deployed. When a medicament delivery is desired, the cover 18 may be opened as shown in FIG. 2 and the needle assembly 30 may be deployed as shown in FIG. 3. Once the medicament has been delivered, the needle assembly 30 may be returned to the chamber 22 and the cover 18 may be closed.

As may also be best seen in FIG. 5, the needle assembly 30 includes a needle 32 that forms a piercing member to deliver the medicament. The needle 32 is housed in a collapsible hood 34 that normally extends beyond the tip 33 of the needle. A source 36 of antiseptic is housed within the hood 34 to maintain the antiseptic condition of the needle 32 between medicament deliveries. The antiseptic source 36 may be a sponge or other suitable filler in which an antiseptic is embedded or impregnated, for example.

The mounting arrangement 40 thus disposes the needle 32 along side the device case 16 pointing toward the patient. As will be seen subsequently, when medicament delivery is desired, the end 35 of the needle assembly 30 is pushed toward the wearer's skin. When the hood 34 contacts the skin, it will collapse, allowing the needle 32 to pierce the patient and deliver the medicament. When medicament delivery is completed, the antiseptic source wipes the needle 32 with antiseptic upon the hood 34 returning to its customary shape to maintain the antiseptic condition of the needle 32. The needle assembly 30 may then be stored within the case 18 as previously described.

FIG. 4 shows the interior of the device 14. The device 14 includes a cylindrical well 51 and a cylindrical piston 52. When the cylindrical piston 52 is spaced from the bottom 56 of the well 51, a reservoir 54 is formed for holding the liquid medicament to be delivered. A threaded ring 60 encircles the well 51. When the ring 60 is turned, a space is formed between a shoulder 62 and the ring 60. This space determines the distance in which the piston 52 will travel during medicament delivery and hence the volume of medicament to be pumped from the reservoir 54 and delivered to the patient. The medicament, during delivery, exits the reservoir 54 at a port 58 and is transferred to the needle 32 by a flexible conduit 50.

A first linkage 70 between the arm 42 and the case 16 and a similar second linkage 72 between the cover 18 and the case 16 causes the piston 52 to move further into the reservoir 54 when the opened cover 18 and the needle assembly 30 are concurrently depressed (FIG. 5). This causes the piston 52 to travel into the reservoir the set distance until the ring 60 is once again contacted by the shoulder 62.

As may be seen in FIG. 6, the ring 60 may be connected to a tab 66 which may be used to turn the ring. The tab 66 together with an indicator 68 on the housing 16 provides an indication of the amount of medicament that has been delivered.

In operation, when a dosage of medication is to be delivered, the cover 18 to the device case 16 is first opened as shown in FIG. 2. This exposes the needle assembly 30. Next, as best illustrated in FIGS. 3 and 5, the needle assembly 30 is released from the chamber 22 and pivoted about the hinges 42 and 44 to render the needle turned downward pointing towards the patient's skin. Next, the ring 60 is turned by engaging the tab 66 (FIG. 6) and displacing it to the desired dose amount. The ring 60 is now displaced from the shoulder 62. The opened cover 18 and the arm 42 are next depressed causing the piston 52 to enter further into the reservoir 54 until the shoulder 62 contacts the ring 60 and a fixed amount of medicament has been delivered. During delivery, the medicament is caused to be displaced from the reservoir 54 by the piston 52 and flows through the port 58 and the conduit 50 to the needle 32. When the arm 42 is depressed, the collapsible hood 34 collapses to permit the needle 32 to pierce the patient's skin and deliver the medicament. After the medicament is delivered, the needle 32 is permitted to retract from the patient. As it does so, it is wiped by the antiseptic source 36 to maintain its antiseptic condition. The needle assembly 30 is then retracted back into the chamber 22 of the device case 16 and the cover 18 is closed.

The device 14 also provides an indicator of the amount of medicament that is left in the device reservoir after the last dosage delivery. More specifically, as may be seen in FIG. 4, after a dose of medicament is delivered the space 63 between the ring 60 and the base 15 of the device 14 provides an indication of the volume of medicament remaining. For a more accurate indication, the number of exposed threads within the space may be counted.

FIG. 7 is a partial sectional side view illustrating the infusion device 114 of another infusion assembly according to another embodiment of the invention. The device 114 includes a reservoir 154 formed by a cylindrical wall 120. The wall 120 has an outer thread 121 that engages an inner thread 161 of a ring 160. Extending into the reservoir 154 and forming a cap of the device 114 is a piston 152. The piston 152 carries a latch assembly 170 that includes a proximal leg 172, a distal leg 178, and a stop 174. The leg 172 has a surface 176 that may carry an indication arrow. The piston 152 further carries a ring turner dog 166 having a surface 167 that abuts the ring 160 when the latch 170 is engaged. The latch 170 is engaged when the leg 172 is pushed inward and locks. The device further includes an outlet 158 through which the medicament flows during delivery.

The device 114 can be used to deliver a set volume of liquid medicament in the following manner. First, the latch 170 is released and rotated in a counter clockwise direction to reset the ring turner dog 166. Next, the latch arm 172 is depressed to cause the leg portion 178 to engage the ring 160. With the ring 160 thus engaged, the latch 170 is turned in the clockwise direction a desired number of degrees which also causes the ring 160 to be rotated the same number of degrees. This creates a space 165 between the ring turner dog surface 167 and the ring 160 representing the travel of the piston 152 into the reservoir when the latch 170 is fully engaged and thus the volume of medicament to be pumped by displacement from the reservoir 154 for delivery. Next, the latch is engaged by pushing the arm 172 down to the locked position to cause the piston 152 to be driven downward until the ring turner dog 166 once again engages the ring 160. Delivery of the desired volume of medicament is now completed. The arrow formed on the surface 176 will be latched and pointing to indicate the volume of medicament last delivered.

Referring now to FIG. 8, it is a sectional side view illustrating an alternative needle assembly that may be employed in the assembly of FIGS. 1-6 according to a further embodiment of the invention. Here it may be seen that the needle 132 is carried by a button 131 that extends through an opening 143 within the arm 142. A spring 135 extends between the button 131 and an inner surface 139 of the collapsible hood 134. The collapsible hood 134 has an opening 133 through which the needle 132 may pass when the medicament is delivered. The hood 134 further contains a source 136 of antiseptic to maintain the antiseptic condition of the needle 132 as previously described.

It may also be noted in FIG. 8 that the button 131 has a shoulder 137 that makes interference fit with the opening 143 of arm 142. Passing there through is a flexible conduit 150 that carries the medicament from the reservoir to the needle 132. When the button 131 is not depressed, the interference fit between the button shoulder 137 and the opening 143 pinches the conduit off to preclude medicament flow. However, when medicament is to be delivered and the button 131 is depressed, the interference fit is resolved and the conduit 150 is no longer pinched off. This permits medicament flow to the needle 132 for delivery. It also assures that medicament will not flow to the needle 132 until after the button 131 is depressed and the needle 132 is thus deployed beneath the patient's skin to deliver the medicament.

While particular embodiments of the present invention have been shown and described, modifications may be made. It is therefore intended in the appended claims to cover all such changes and modifications which fall within the true spirit and scope of the invention as defined by those claims.

What is claimed is:

1. A wearable liquid medicament delivery assembly comprising:
   a band arranged to at least partially encircle and be secured to a body extremity of a wearer; and
   a liquid medicament delivery device carried by the band, the device including a reservoir arranged to hold the liquid medicament, a piercing member arranged to penetrate the skin of the wearer to deliver the liquid medicament, and a pump that pumps the liquid medicament from the reservoir to the piercing member to thereby cause the liquid medicament to be delivered to the wearer,
   wherein the device further includes a dosage selector that adjusts the device to deliver a selectable volume of liquid medicament.

2. The assembly of claim 1, wherein the device includes a needle assembly including the piercing member, and wherein the piercing member comprises a needle.

3. The assembly of claim 2, wherein the device includes a mounting for the needle assembly and wherein the mounting is arranged to deploy the needle prior to each liquid medicament delivery and to retract the needle after each liquid medicament delivery.

4. The assembly of claim 3, wherein the needle assembly includes a source of antiseptic that maintains the needle in an antiseptic condition.

5. The assembly of claim 3, wherein the needle assembly includes a collapsible boot that houses the needle.

6. The assembly of claim 5, wherein the needle assembly includes a source of antiseptic within the collapsible boot that maintains the needle in an antiseptic condition.

7. The assembly of claim 6, wherein the source of antiseptic within the collapsible boot comprises a filler with the antiseptic embedded therein.

8. The assembly of claim 1, wherein the device is attachable to and detachable from the band.

9. The assembly of claim 3, wherein the mounting includes an arm that aligns the needle assembly with the skin of the wearer.

10. The assembly of claim 1, wherein the dosage selector retains an indication of the selected volume after liquid medicament delivery.

11. The assembly of claim 10, wherein the dosage selector includes a latch that retains an indication of the selected volume after liquid medicament delivery.

12. The assembly of claim 1, wherein the device further includes a safety valve that precludes liquid medicament flow to the piercing member until the piercing member has penetrated the skin and has been deployed.

13. The assembly of claim 1, wherein the device further includes a flexible conduit coupling the reservoir with the piercing member.

14. The assembly of claim 1, wherein the pump includes a piston that displaces the liquid medicament from the reservoir.

15. The assembly of claim 1, wherein the device further includes an indicator that indicates a remaining amount of medicament in the reservoir after medicament delivery to the wearer.

16. A wearable liquid medmedicament delivery assembly of comprising:
   a liquid medicament delivery device including a reservoir arranged to hold the liquid medicament, a needle arranged to penetrate the skin of the wearer to deliver the liquid medicament, and a pump that pumps the liquid medicament from the reservoir to the piercing member to thereby cause the liquid medicament to be delivered to the wearer; and
   a band arranged to be secured to a body of a wearer and to carry the device,
   wherein the device further includes a dosage selector that adjusts the device to deliver a selectable volume of liquid medicament.

17. The assembly of claim 16, wherein the device includes a housing secured to the band, wherein the needle is enclosable within the housing, and wherein the needle is releasable from the housing for liquid medicament delivery to the wearer.

18. The assembly of claim 17, wherein the device further includes a cover arranged to cover the housing with the needle enclosed therein and to open to permit release of the needle for liquid medicament delivery to the wearer.

19. The assembly of claim 18, wherein the device further includes a mount having a distal end supporting the needle and a proximal end hingedly connected to the housing to permit the needle to pivot from an enclosed position within the device housing to a ready position for liquid medicament delivery to the wearer.

20. The assembly of claim 19, wherein the needle is arranged to be displaced from the ready position to a delivery position penetrating the skin of the wearer for the delivery of liquid medicament to the wearer.

21. The assembly of claim 20, wherein the device further includes a collapsible boot encircling the needle.

22. The assembly of claim 21, further comprising a source of antiseptic within the collapsible boot that maintains the needle in an antiseptic condition.

23. The assembly of claim 22, wherein the source of antiseptic within the collapsible boot comprises a filler with the antiseptic embedded therein.

24. The assembly of claim 20, wherein the device further includes a flexible conduit coupling the reservoir with the needle.

25. The assembly of claim 24, wherein the device further includes a safety valve that precludes liquid medicament flow to the needle until the needle has penetrated the skin.

26. The assembly of claim 25, wherein the safety valve is arranged to pinch the flexible conduit closed to preclude liquid medicament flow to the needle until the needle has penetrated the skin.

27. The assembly of claim 16, wherein the device further includes a dosage indicator that provides an indication of a total number of liquid medicament dosages delivered.

28. The assembly of claim 16, wherein the pump includes a piston that displaces the liquid medicament from the reservoir.

* * * * *